United States Patent [19]

Kurtz et al.

[11] Patent Number: 4,619,647
[45] Date of Patent: Oct. 28, 1986

[54] SURGICAL DRAINAGE APPARATUS

[75] Inventors: Leonard D. Kurtz, Woodmere; Joseph M. LiCausi, Port Jefferson Station, both of N.Y.

[73] Assignee: BioResearch Inc., Farmingdale, N.Y.

[21] Appl. No.: 766,012

[22] Filed: Aug. 15, 1985

Related U.S. Application Data

[62] Division of Ser. No. 606,968, May 4, 1984.

[51] Int. Cl.⁴ .............................................. A61M 1/00
[52] U.S. Cl. .................................. 604/318; 604/319; 604/320
[58] Field of Search ........................ 137/512, 526, 539; 604/318, 319, 320

[56] References Cited

U.S. PATENT DOCUMENTS

| | | | |
|---|---|---|---|
| 2,145,148 | 11/1938 | Roy | 604/319 |
| 2,809,659 | 10/1957 | Gillespie et al. | 137/526 |
| 2,903,014 | 9/1959 | Sheppard | 137/539 |
| 3,363,626 | 1/1968 | Bidwell et al. | 604/318 |
| 3,672,396 | 6/1972 | Pauliukonis | 137/539 |
| 3,750,692 | 8/1973 | Tibbs | 604/318 |
| 3,982,595 | 12/1970 | Coulter | 137/539 |
| 3,989,172 | 1/1980 | Whitmore | 137/539 |
| 4,184,510 | 1/1980 | Murry et al. | 137/512 |
| 4,261,362 | 4/1981 | Kurtz et al. | 604/320 |
| 4,396,386 | 8/1983 | Kurtz et al. | 604/318 |

Primary Examiner—John F. Niebling
Assistant Examiner—Terryence Chapman
Attorney, Agent, or Firm—Larson and Taylor

[57] ABSTRACT

A surgical pleural drainage apparatus for draining fluids from the body of a patient is disclosed. The apparatus includes a container with a collection chamber. A suction outlet is provided on the container which is connected to a source of negative pressure and a fluid passageway connects the suction outlet to the collection chamber. A non-liquid one-way valve is provided in the fluid passageway for allowing fluid flow only from the collection chamber to the suction outlet. An air leak indicator is also provided in the passageway to indicate a flow of gases through the passageway and optionally the qualitative quantity of that flow. Preferably, the air leak indicator includes a visible liquid trap through which any gases flow and form bubbles which are visible. The liquid trap is prefilled with glycerine or a like liquid. The amount of negative pressure applied to the collection chamber is controlled by a suction control device. An excess negative pressure relief device and a positive pressure relief device are also provided for the collection chamber. Preferably, a pressure measuring device is provided for measuring the negative pressure in the passageway and a dynamic pressure measuring device is provided for measuring the pressure changes in the collecting chamber during respiration.

5 Claims, 11 Drawing Figures

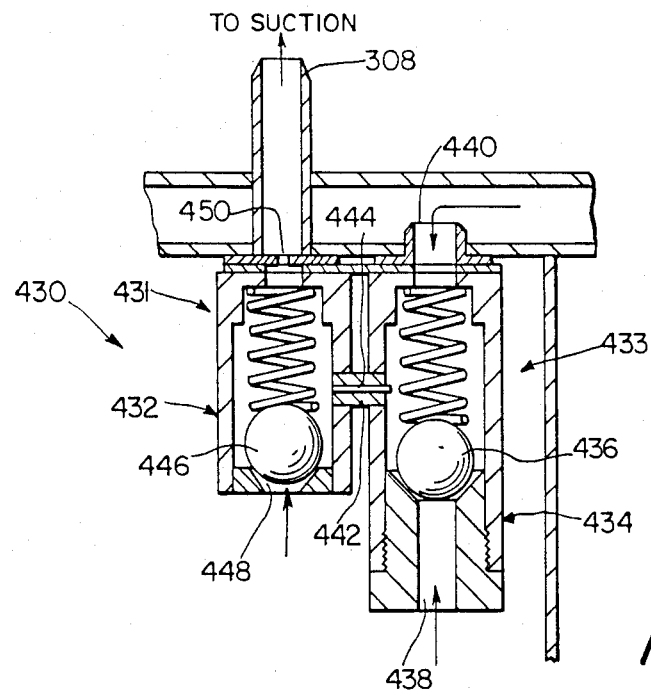
FIG. 9
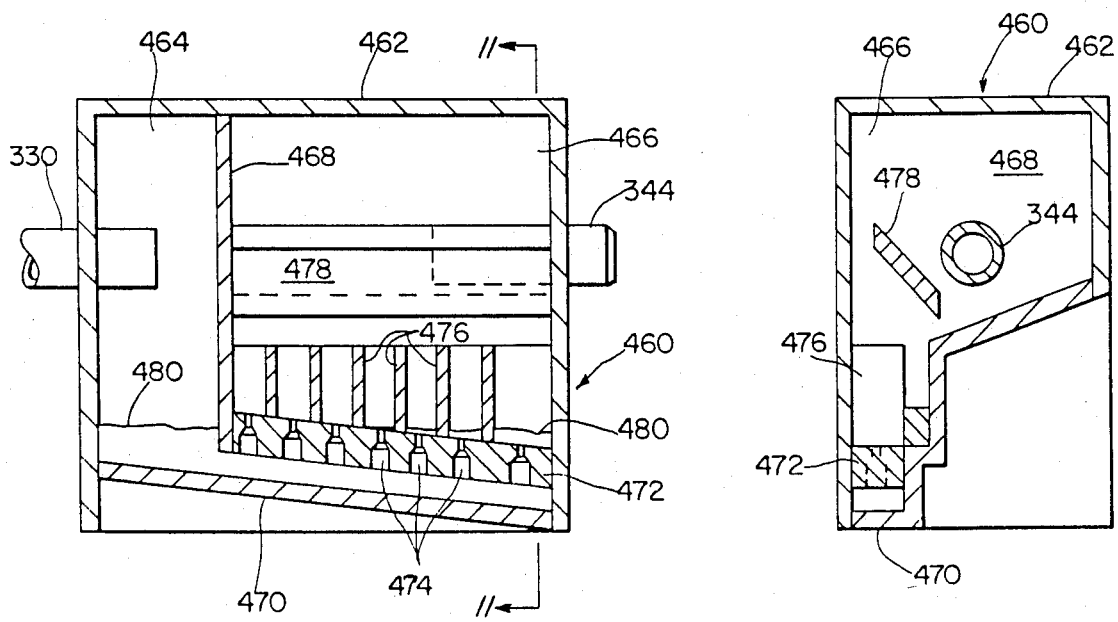
FIG. 10
FIG. 11

SURGICAL DRAINAGE APPARATUS

This is a division of application Ser. No. 606,968 filed May 4, 1984.

FIELD OF THE INVENTION

The present invention relates generally to surgical drainage devices which are used in draining fluids from the body, e.g. the pleural cavity.

BACKGROUND OF THE INVENTION

It is essential for normal breathing that the space within the pleural cavity surrounding the lungs be free of liquid and be subject to negative pressure so as to draw the lungs outwardly to fill this pleural cavity in order to permit optimal breathing. Any invasion of the pleural cavity such as caused by lung surgery or foreign objects which pierce the rib cage or such as occur, for example, when the patient has pleurisy, generates fluids in the pleural cavity which tend to obstruct normal breathing. It is thus necessary to provide a device which can remove these fluids from the pleural cavity and at the same time insure that the desired degree of negative pressure is maintained within the pleural cavity.

One of the basic types of apparatus which has been used for this purpose is shown, for example, in U.S. Pat. Nos. 3,363,626 and 3,363,627. This apparatus is known as an underwater drainage apparatus and provides three chambers, one chamber comprising a collection chamber for collecting the fluids drained from the pleural cavity through a thoracotomy tube, a second chamber known as an underwater seal chamber which protects the pleural cavity from being subject to atmospheric pressure, and a third chamber known as a pressure manometer chamber which serves to regulate the degree of negative pressure within the pleural cavity. This type of apparatus has been highly successful in both removing fluids from the pleural cavity and in maintaining the desired degree of negativity within the pleural cavity.

However, an apparatus such as disclosed in the patents referred to above requires prefilling of the underwater seal chamber with water as well as prefilling of the pressure manometer chamber to the desired level to maintain the desired degree of negativity within the pleural cavity. It is obvious that it would desirable to eliminate the need for filling the underwater seal and manometer chambers, particularly in emergency situations but also in general use. This is because the less the user of the apparatus has to do with the operation the less likely it is that something will be done improperly, i.e. the greater the active participation the greater the chance for human error. For this reason, drainage devices have been developed which do not require a filling of the underwater seal chamber. Examples of such devices are disclosed in U.S. Pat. Nos. 4,015,603 and 4,396,386. However, an underwater seal must still be formed using the liquids drained from the body of the patient.

The latter patent referred to above also discloses a manually adjustable control valve to regulate the negative pressure applied in the collection chamber and a bellows for indicating the amount of negative pressure within the collection chamber. A means for controlling the negative pressure in a collection chamber is also disclosed in U.S. Pat. No. 4,372,336. The means disclosed is a diaphragm which is movable into position on the suction outlet of the device whenever the applied suction is too great.

SUMMARY OF THE INVENTION

In accordance with the present invention, a surgical pleural drainage apparatus for draining fluids from the body of a patient is provided. The apparatus includes a container with a collection chamber formed therein. The collection chamber is used to collect fluids received through a fluid inlet in the container from the body of the patient. A connection means is provided for connecting the collection chamber to a source of negative pressure so that a negative pressure or suction is created within the collection chamber to draw fluids into the collection chamber through the fluid inlet. The connecting means includes a suction outlet mounted on the container and a fluid passageway which connects the suction outlet with the collection chamber. A non-liquid passageway one-way valve means is provided in the passageway for allowing fluid flow only from the collection chamber to the suction outlet. An air leak indicating means is also provided in the passageway for indicating the directional flow of any gases through the passageway and optionally the qualitative quantity of these gases. A suction control means is further provided in the passageway for controlling the amount of negative pressure applied to the collection chamber. This control means holds the pressure applied to the collection chamber at a relative constant despite changes in wall suction varying from 30 mmHg to 500 mmHg.

In the preferred embodiment of the present invention, the air leak indicating means includes a liquid trap which is visible through the container. Thus as any gases flow therethrough, bubbles are formed which serve as visible indicators of such a flow and of a patient air leak. An excess negative relief means for relieving excess negative pressure in the collection chamber and a positive pressure relief means for relieving positive pressure in the collection chamber are also provided. Preferably, the excess negative pressure relief means, when activated, permits the flow of air at atmospheric pressure through a filter of about 0.45 microns into the collection chamber until the pressure in the collection chamber is approximately $-10$ cmH$_2$O, at which pressure the negative pressure relief valve is automatically inactivated out of the control of the operator. The negative pressure in the collection chamber must be greater than $-10$ cmH$_2$O before the negativity relief valve will allow air flow into the collection chamber.

In the preferred embodiment, a pressure measuring means for measuring the negative pressure in the passageway is also provided. The pressure measuring means includes a vertically disposed straight bore having two adjoining tapered slots. A ball is disposed in the bore. The ball rises in the bore to a position dependent on value of the source of negative pressure.

In one preferred embodiment, the control means includes a fine pressure adjusting means including a first chamber having a resiliently biased fine one-way valve disposed therein. The first chamber is divided by the valve into a vent side which is vented to atmosphere and a suction side which forms a portion of the passageway. A gross pressure adjusting means including a second chamber is provided which has a resiliently biased gross one-way valve disposed therein. This gross one-way valve divides the second chamber into a vent side which is vented to atmosphere and a suction side forming a portion of the passageway downstream of the suction side of the first chamber. The suction side of the second chamber is also connected to the suction side of the first chamber through a restricted opening. In this manner, fluid flow is allowed from the vent side to the suction side of the second chamber only when the negative pressure in the suction side exceeds a value somewhat greater than the desired value of negative pressure in the passageway. Preferably, the suction side of the second chamber is connected directly to the suction outlet and a restrictor is also provided in the suction outlet so that the negative pressure applied by the source of suction to the suction side of the second chamber is reduced by the restrictor.

In an alternative embodiment of the present invention, the control means includes a suction varying means for varying the amount of negative pressure applied to the collection chamber relative to the negative pressure applied at the suction outlet. The suction varying means includes a plurality of resiliently biased valve means arranged in a series with the outlet of one valve means connected to the inlet of the next valve means. The initial inlet of the first valve means in the series is vented to atmosphere while the last outlet of the valve means in the series is connected to the suction outlet. A passage is also provided from each respective outlet to the suction outlet through a valve selector which can be adjusted to fluidly connect one of the respective outlets with the suction outlet. In this manner, depending on the outlet selected by the selector, the rate of flow of bleed air to the suction outlet and hence the negative pressure at the suction outlet is adjusted so that the amount of negative pressure which is applied to the collection chamber is adjusted.

According to the preferred embodiment, a dynamic pressure measuring means is also provided for measuring pressure changes in the collection chamber and hence the changes in pressure in the collection chamber as the patient breathes. Preferably, the dynamic pressure measuring means includes a bellows whose interior region is fluidly connected to the collection chamber and whose exterior region is fluidly connected to the passageway.

Other features and advantages of the invention are stated in or apparent from a detailed description of presently preferred embodiments of the invention found hereinbelow.

BRIEF DESCRIPTION OF THE DRAWINGS

FIG. 9 is a cross-sectional front elevation view of an alternative embodiment of a pressure control.

FIG. 10 is a cross-sectional front elevation view of a patient air leak meter usable in the bubble chamber of the device depicted in FIG. 5.

FIG. 11 is a cross-sectional side view of the air leak meter depicted in FIG. 10 taken along the line 11—11.

DETAILED DESCRIPTION OF THE PREFERRED EMBODIMENTS

Figure 1:
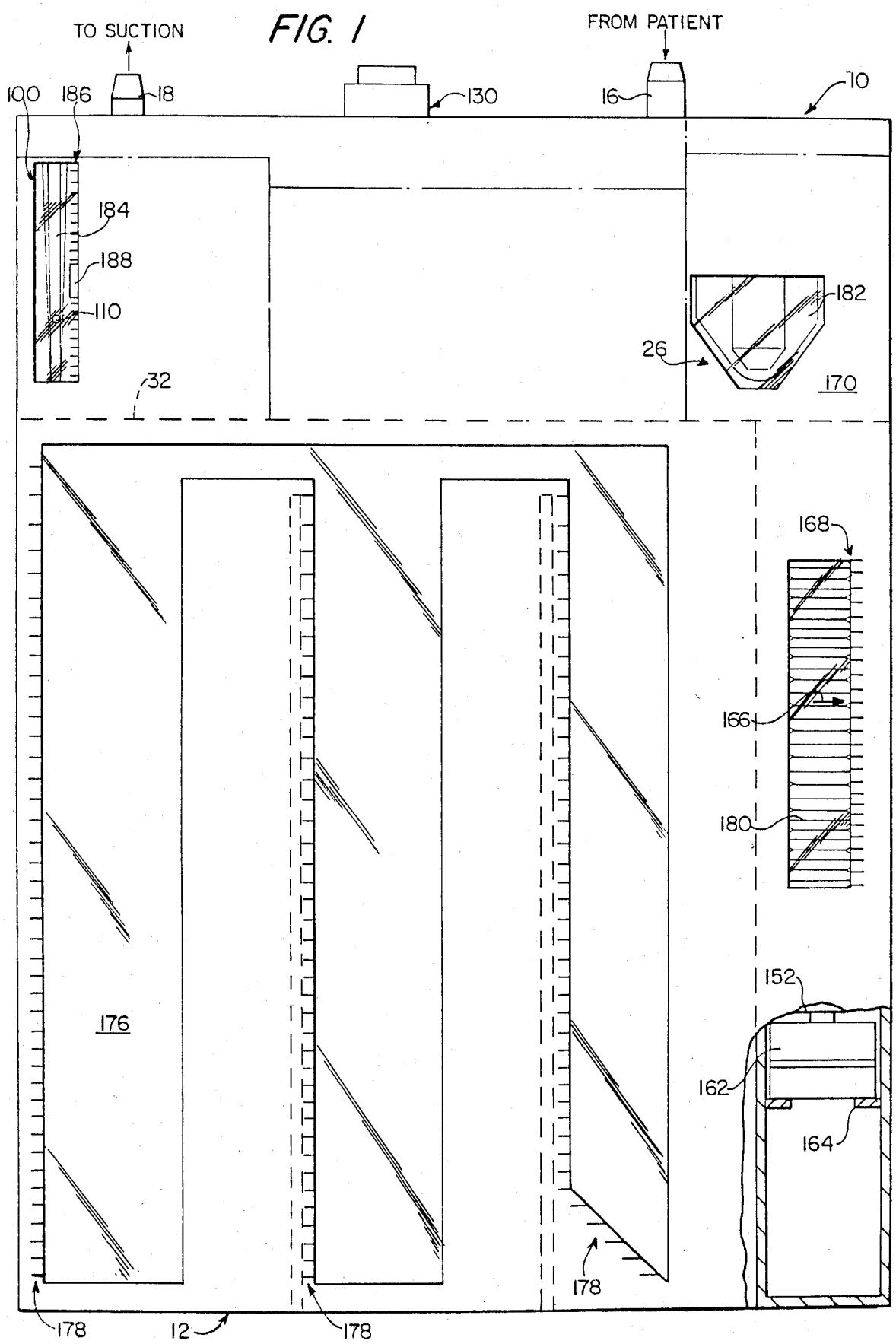
FIG. 1 is a front elevation view of a surgical pleural drainage apparatus according to the present invention.
Figure 2:
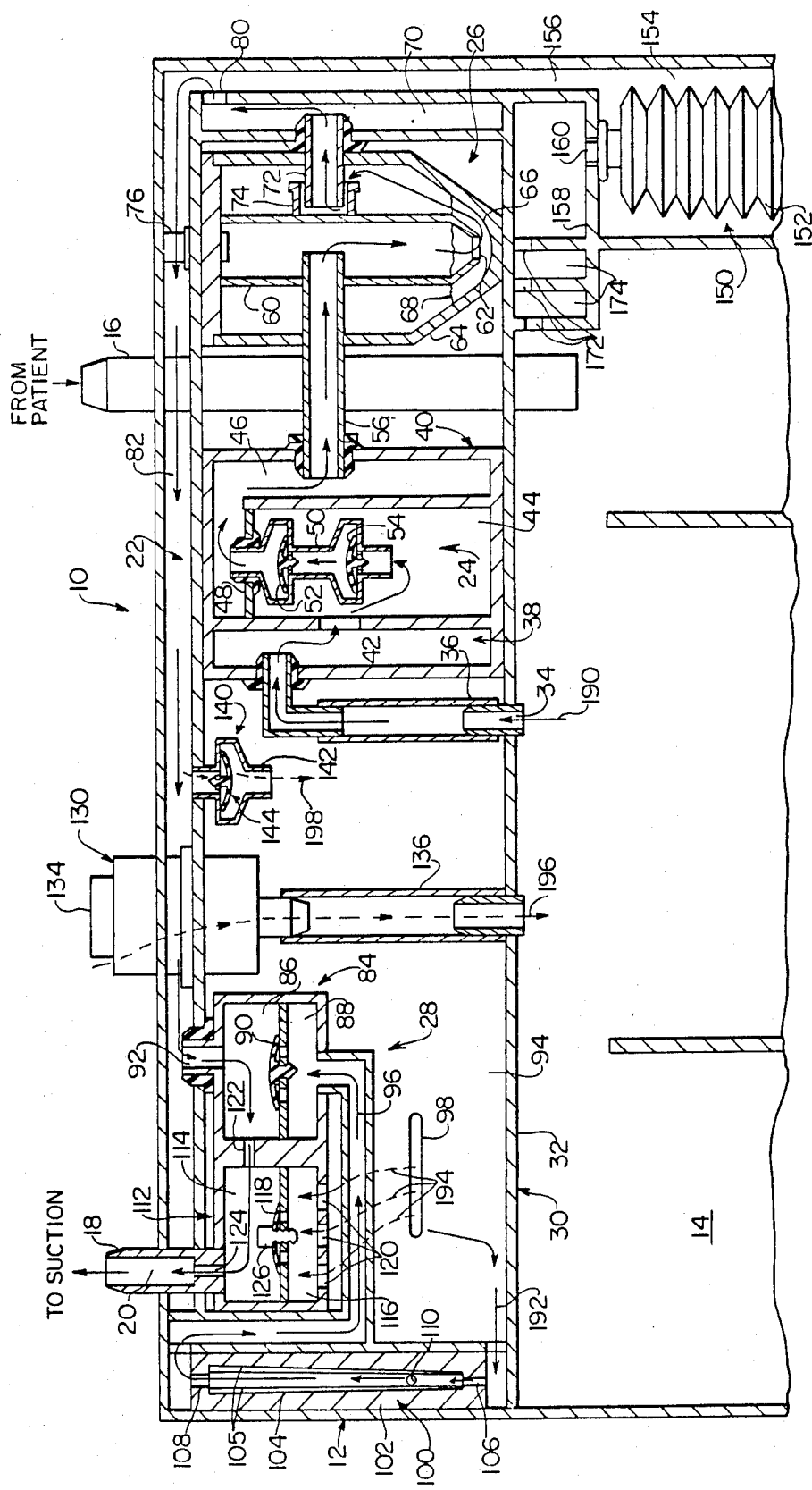
FIG. 2 is a front elevation view in cross section of the upper portion of the drainage apparatus depicted in FIG. 1.

With reference now to the drawings in which like numerals represent like elements throughout the views, a surgical pleural drainage apparatus 10 is depicted in FIGS. 1 and 2. Drainage apparatus 10 includes a container 12 in which a collection chamber 14 is provided. As shown, collection chamber 14 is divided into three connected compartments so that the liquids collected therein are easily measured by suitable indicia 178 provided on the front of container 12. Located immediately above the first compartment is a fluid inlet 16 which extends through collection chamber 14 to the top of container 12. Fluid inlet 16 is suitably connected to the patient by a thoracotomy tube (not shown) or the like to conduct fluids drained from the patient into collection chamber 14.

Container 12 also includes a suction outlet 18 which is suitably connected to a source of suction or negative pressure. As shown, the base of suction outlet 18 includes a restricted bore 20. Suction outlet 18 is fluidly connected to collection chamber 14 via a passageway 22 which includes a non-fluid passageway one-way valve means 24, an air leak indicating means 26, and a control means 28.

As shown best in FIG. 2, container 12 is divided into collection chamber 14 and an upper chamber 30 by an interior wall 32. Passageway 22 begins at interior wall 32 where a suction inlet 34 is located. Connected to suction inlet 34 is a short passage 36 which terminates in a tell-tale chamber 38. Should any liquids inadvertently be withdrawn through suction inlet 34, the liquids accummulate in the bottom of tell-tale chamber 38 and serve as a visible indication of a malfunction of drainage apparatus 10.

Tell-tale chamber 38 is fluidly connected to a valve chamber 40 through a bore 42 as shown. Valve chamber 40 is divided into an inlet side 44 and an outlet side 46 by a wall 48. One-way valve means 24 fluidly connects inlet side 44 to outlet side 46. One-way valve means 24 includes a valve seat member 50 in which two umbrella valves 52 and 54 are arranged in series. Alternatively, one-way valve means 24 could include appropriate ball and spring one-way valves. The purpose of one-way valve means 24 is to allow fluid flow in passageway 22 only from suction inlet 34 to suction outlet 18 and to prevent any reverse fluid flow in passageway 22.

A short passage 56 is used to fluidly connect outlet side 46 of valve chamber 40 with air leak indicating means 26. As shown, short passage 56 terminates in a vertically disposed tube 60 having a bottom outlet 62. Tube 60 is disposed in air leak chamber 64 having a concave bottom 66 which is adjacent outlet 62. A small volume of a suitable liquid 68, such as glycerine, is provided in air leak chamber 64 to a height slightly above outlet 62 in tube 60. Liquid 68 preferably has a high vapor pressure so that liquid 68 does not readily evaporate.

Air leak chamber 64 is fluidly connected to a passage chamber 70 by a short passage 72. As shown, one end of short passage 72 is adjacent tube 60 and is surrounded by a collar 74 which is attached to tube 60. Collar 74 is spaced slightly from the end of short passage 72 such that an air gap is provided for fluid flow. It should be appreciated that no matter how drainage apparatus 10 is tipped, liquid 68 cannot enter and pass through short passage 72. It should further be appreciated that no matter how drainage apparatus 10 is tipped, liquid 68 cannot enter the end of short passage 56 provided in tube 60 either.

A sealed tube 76 is also provided between the top of tube 60 and the exterior of container 12. Sealed tube 76 is sealed by a rubber diaphragm (not shown) so that no fluids pass through seal tube 76. However, should it be desired to add any addition liquid 68 to air leak chamber 64, a hypodermic needle can be temporarily extended through sealed tube 76 to supply the desired additional quantity of liquid 68.

Passage chamber 70 includes an exit bore 80 which opens into an elongate passage 82 along the top of container 12. Elongate passage 82 fluidly connects passage chamber 70 with control means 28.

Control means 28 includes a fine or primary control chamber 84 which is separated into a suction side 86 and a vent side 88 by an umbrella valve 90. As shown, suction side 86 is connected to elongate passage 82 by a short passage 92. Vent side 88 is connected to a vent chamber 94 by an elongate passage 96. Vent chamber 94 includes a slot 98 in the back wall by container 12 by which vent chamber 94 is maintained at substantially atmospheric pressure.

Located in a vertical section of elongate passage 96 is a pressure measuring means 100. Pressure measuring means 100 includes a member 102 having an elongate bore 104 therein. Located at the bottom of bore 104 is a restricted opening 106 which has a much smaller diameter than bore 104. Located at the top of bore 104 is an opening 108 which has a diameter about the same as bore 104 at that point. As shown in FIG. 2, bore 104 is provided with a pair of opposed, tapered slots 105 extending along and open to bore 104. Disposed within bore 104 is a ball 110. Ball 110 rises in bore 104 depending upon the volume of bleed air conducted through bore 104.

Disposed adjacent to fine or primary control chamber 84 is a gross or secondary control chamber 112. Secondary control chamber 112 is divided into a suction side 114 and a vent side 116 by an adjustable umbrella valve 118. As shown, vent side 116 includes three openings 120 by which vent side 116 is vented to vent chamber 96 and hence to atmosphere. A restricted opening 122 fluidly connects suction side 114 with suction side 86 of primary control chamber 84. Suction side 114 is also connected to suction outlet 18 and restricted bore 20 through opening 124. It should be appreciated that screw 126 which attaches adjustable umbrella valve 118 to the dividing wall in secondary control chamber 112 is turned to vary the pressure differential necessary for adjustable umbrella valve 118 to open. Use of this adjusting feature will described subsequently.

Figure 6:
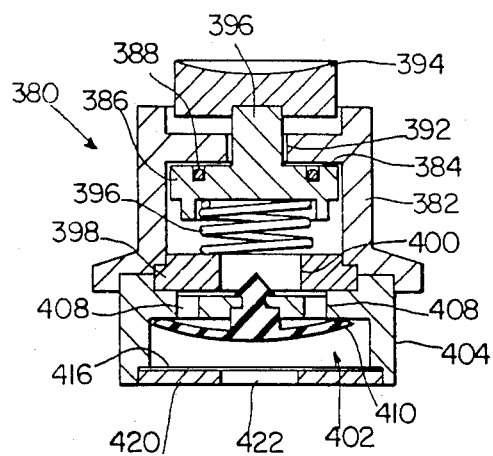
FIG. 6 is a front elevation view in cross section of the negative pressure relief valve depicted in FIGS. 1 and 5.
Figure 7:
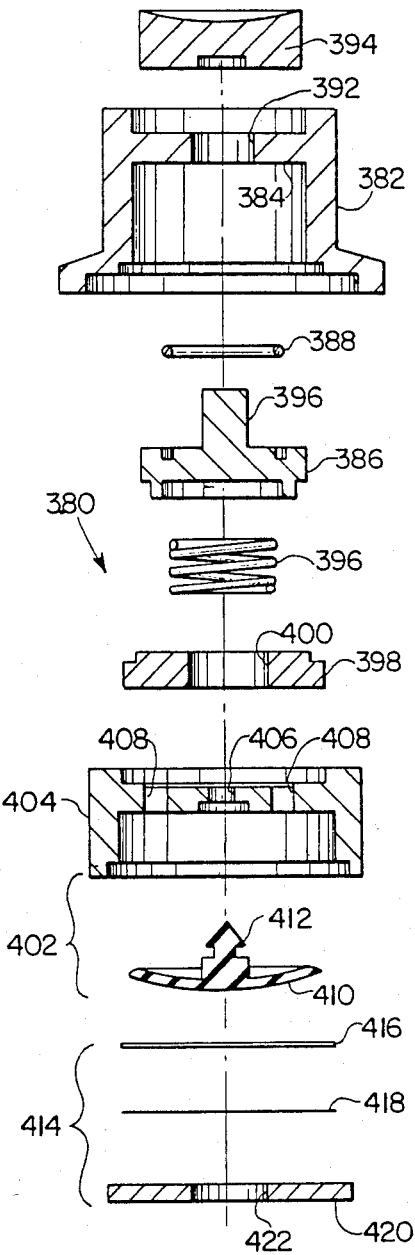
FIG. 7 is an exploded cross-sectional elevation view of the negative pressure relief valve depicted in FIG. 6.
Figure 8:
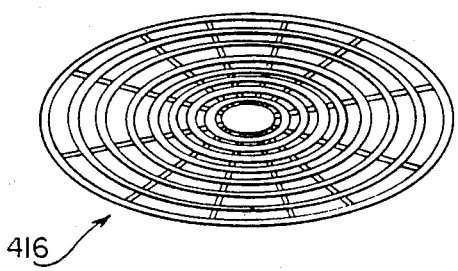
FIG. 8 is a perspective view of the filter cover depicted in FIG. 7.

Drainage apparatus 10 is also provided with an excess negative pressure relief means 130 which is shown in greater detail in FIGS. 6, 7 and 8. Excess negative pressure relief means 130 is used to relieve excess negativity which can occur in collection chamber 14. Preferably, excess pressure relief means 130 is actuated by a push button 134. Excess negative pressure relief means 130 is connected to collection chamber 14 through a passage 136 as shown. Details of a suitable excess negative pressure relief means 130 are discussed subsequently. By actuation of push button 134, atmospheric air is permitted to flow into collection chamber 14 to relieve any excess negativity therein.

Drainage apparatus 10 is further provided with a positive pressure relief means 140. Positive pressure relief means 140 is used to relieve any positive pressures which are inadvertently created in collection chamber 14 and hence in elongate passage 82. As shown in FIG. 2, positive pressure relief means 140 includes a passage 142 which extends from elongate passage 82 to vent chamber 94 and in which an umbrella valve 144 is disposed. Umbrella valve 144 is designed to open only when a predetermined positive pressure exists in elongate passage 82 so that this undesired positive pressure is vented to atmosphere through vent chamber 94. Otherwise, umbrella valve 144 prevents any reverse flow of atmospheric air into elongate passage 82.

A dynamic pressure measuring means 150 is also provided in drainage apparatus 10 for measuring the changes in pressure in collection chamber 14 as the patient breathes. Dynamic pressure measuring means 150 includes a bellows 152 disposed in a bellows chamber 154. Bellows chamber 154 is fluidly connected to elongate passage 82 by a passage 156. As shown in FIG. 2, bellows 152 is suspended from a horizontal wall 158 having an opening 160 therein. At the bottom of bellows 152 is a small weight 162 which normally rest against a stop 164 prior to the actuation of drainage apparatus 10.

As shown in FIG. 1, bellows 152 also includes an indicator 166 and indicia 168 located adjacent indicator 166 on face 170 of container 12. The instantaneous pressure in collection chamber 12 is transferred to the interior of bellows 152 through openings 172 in tell-tale chambers 174. Should container 12 be tipped such that liquids enter tell-tale chambers 174, some of the liquids are left in tell-tale chambers 174 so that a malfunction of drainage apparatus 10 is indicated thereby. It should be appreciated that the interior of bellows 152 is fluidly connected to collection chamber 14 and the instantaneous changes in pressure which occur therein as the patient breathes. The exterior of bellows 152 is also fluidly connected to collection chamber 14 but only through a tortuous path including flow indicating means 26 and passageway one-way valve means 24. For that reason, the change in pressure which occurs in passage 158 and hence on the exterior of bellows 152 is not instantaneous but is delayed sufficiently to allow bellows 152 to expand or contract with the increases or decreases of pressure in collection chamber 14 as the patient breathes. Thus, the movement of indicator 166 relative to indicia 168 provides an easy determination of the changes in pressure in collection chamber 14 as the patient breathes. Bellows 152 also indicates excessive negative pressure which may be due to striping or the patient gasping for breath.

As shown in FIG. 1, face 170 of drainage apparatus 10 includes a number of transparent sections so that the operation of drainage apparatus 10 can be observed. Thus, clear section 176 is provided over the three columns making up collection chamber 14 so that the filling of collection chamber 14 with liquids is observed. For this reason, indicia 178 is provided adjacent to the columns of collection chamber 14 to allow the amount of liquids collected to be measured. In the same manner, a clear section 180 is provided over indicator 166 on bellows 152 so that the movement of indicator 166 is seen. As indicated previously, indicia 168 is provided adjacent clear section 180.

A clear section 182 is also provided in face 170 in front of flow indicating means 26. The bubbling of gases through liquid 68 is then easily seen through clear section 182. Finally, a clear section 184 is also provided in front of pressure measuring means 100 so that the movement of ball 110 in bore 104 is observed. Indicia 186 is located adjacent clear section 184 so that the pressure in collection chamber 14 is determined by the movement of ball 110. Conveniently, a band 188 of indicia 186 is designated which is the desired location of ball 110 and indicates the proper suction or negative pressure in collection chamber 14.

In operation, drainage apparatus 10 functions in the following manner. Initially, it is noted that drainage apparatus 10 is provided in a sterile package and conveniently includes a hose (not shown) attached to suction outlet 18 which is connected to a source of suction and a separate thoracotomy hose (not shown) attached to fluid inlet 16 which is fluidly connected to the pleural cavity of the patient to be drained. In addition, container 12 is provided with liquid 68 already located in seal chamber 64. As discussed above, seal chamber 64 is constructed such that liquid 68 cannot be spilled therefrom during transport and storage of container 12, no matter how container 12 is oriented or shifted. In addition, screw 126 has been adjusted during manufacture to bias adjustable umbrella valve 118 so that a predetermined negative pressure in suction side 114 is necessary to open adjustable umbrella valve 118 to allow fluid flow from the atmosphere to suction side 114.

After suction outlet 18 is connected to a source of suction or negative pressure and fluid inlet 16 is connected to the pleural cavity of the patient, a negative pressure is created in collection chamber 14. As shown in FIG. 2, liquids and gases from the patient are drawn into collection chamber 14 through tube 16. The negative pressure created in collection chamber 14 is provided by the withdrawal of gases from suction inlet 34 through passageway 22 to suction outlet 18. This flow of gases is indicated generally by arrowed line 190. Thus, gases flow from collection chamber 114 through short passage 36 to tell-tale chamber 38. If container 12 were tipped so that liquids were drawn into short passage 36, any liquids passing further than passage 36 are indicated by an accumulation of the liquids at the bottom of tell-tale chamber 38.

The withdrawn gases are next passed through one-way valve means 24 which prevents any reverse flow of fluids so that an inadvertent loss of negative pressure at suction outlet 18 does not cause collection chamber 14 to immediately lose the negative pressure present therein. The withdrawn gases are next passed through short passage 56 to flow indicating means 26. As the gases enter tube 60, the gases are drawn through liquid 68 causing bubbling therein before passing through short passage 72. As shown in FIG. 1, the bubbling of the gases through liquid 68 is easily seen from the front of drainage apparatus 10 through clear section 182. No bubbling through liquid 68 indicates a proper operation of drainage apparatus 10. However, continuous bubbling through liquid 68 indicates either an air leak in the connections in container 12 or an air leak in the pleural cavity of the patient. In either event, persistent bubbling acts as an indicator that something is wrong and needs to be corrected. If for some reason liquid 68 is not at a sufficient height in air leak chamber 64, additional liquid is injected through seal tube 76.

From short passage 72, the withdrawn gases pass through elongate passage 82 to suction side 86 of primary control chamber 84 which forms part of control means 28. The suction or negative pressure created in suction side 86 causes umbrella valve 90 to open when the suction exceeds a predetermined value. For example, umbrella valve 90 can be selected so as to open when the suction in suction side 86 is approximately −20 centimeters of water. When the suction is greater than −20 centimeters of water, air is withdrawn from atmosphere through slot 98 in vent chamber 94 as indicated by arrow line 192. This air is further withdrawn through bore 104 and pressure measuring means 100 to elongate passage 96, vent side 88, and finally around umbrella valve 90 to suction side 86. As air is drawn through bore 104, ball 110 is caused to rise in bore 104 to a distance which is proportional to the volume of air flow through bore 104. This rising of ball 110 is due to the increasing size of slots 105 in bore 104. The position of ball 110 is seen through clear section 184 on face 170 of container 12. By use of indicia 186, the suction or negative pressure in suction side 86 and in collection chamber 14 is measured by the position of ball 110. Where the value of the suction applied to suction outlet 18 is variable, this suction source is varied until ball 110 rises to a position adjacent band 188 so that the proper suction in collection chamber 14 is indicated.

From suction side 86 of primary control chamber 84, the withdrawn gases pass through restricted opening 122 into suction side 114 of secondary control chamber 112. From suction side 114, the gases pass through restricted bore 20 to suction outlet 18 and from there to the source of negative pressure. The suction or negative pressure exerted by the source of negative pressure is exerted directly on suction side 114 of secondary control chamber 112. If this negative pressure is too great, adjustable umbrella valve 118 opens to allow atmospheric air to bleed from vent chamber 94 into vent side 116 of secondary control chamber 112 and thence past umbrella valve 118 to suction side 114.

The pressure differential necessary to open adjustable valve 118 is adjustable by advancing or withdrawing screw 126 from the mounting wall. As mentioned above, the adjustment of screw 126 is preferably done at manufacture so that umbrella valve 118 opens at a predetermined pressure. For example, umbrella valve 118 can be adjusted to open where the suction created in suction side 114 is somewhat greater than −20 centimeters of water, −40 centimeters of water, or −60 centimeters of water. In any event, when umbrella valve 118 opens, the flow of atmospheric air to suction side 114 as indicated by arrow lines 194 is relatively unrestricted until this flow is throttled down by restricted bore 20 and opening 124. Thus, the flow of atmospheric air to suction side 114 is sufficient to significantly lower the suction or negative pressure created there to a value slightly greater than that desired in collection chamber 14.

It should be appreciated that the suction side 114 maintains a negative pressure in suction side 86 of primary control chamber 84 as well. This negative pressure is preferably sufficient to open umbrella valve 90 so that atmospheric air is withdrawn from vent chamber 94 through pressure measuring means 110. As mentioned above, umbrella valve 90 is designed to open so as to maintain the desired negative pressure in collection chamber 14. The additional flow of atmospheric air around umbrella valve 90 is sufficient to lower the negative pressure applied from suction side 114 of secondary control chamber 112 to the desired negative pressure for collection chamber 14.

After operation has commenced, a relatively constant negative pressure is created in collection chamber 14 and in elongate passage 82. As mentioned above, the interior of bellows 152 is connected directly to collection chamber 14 while the exterior of bellows 152 is connected directly to elongate passage 22. When the patient breathes, slight changes in pressure occur in collection chamber 14. As this occurs, bellows 152 and indicator 166 move to indicate this breathing. By use of indicia 168 and the movement of indicator 166, the respiratory cycle pressures of the patient are determined.

If excess negative pressure is exerted in collection chamber 14, such as by milking of the thoracotomy tube or other extraneous manipulations, the excess negative pressure is indicated by bellows 152 and is relieved by use of excess pressure relief means 130. To accomplish this, push button 134 is depressed to allow the flow of atmospheric air as indicated by arrow line 196 into collection chamber 14 through passage 136. Push button 134 is depressed until the negative pressure in collection chamber 114 is returned to the proper value at which time excess negative pressure relief means 130 automatically ceases to function as explained subsequently.

Where an undesired positive pressure is inadvertently applied to collection chamber 14 and hence elongate passage 82, this positive pressure is automatically relieved by use of positive pressure relief means 140. Thus, the positive pressure in collection chamber 14 and elongate passage 82 causes umbrella valve 144 to open so that gases in collection chamber 14 pass to atmosphere through slot 98 as indicated by dotted line 198.

Figure 3:
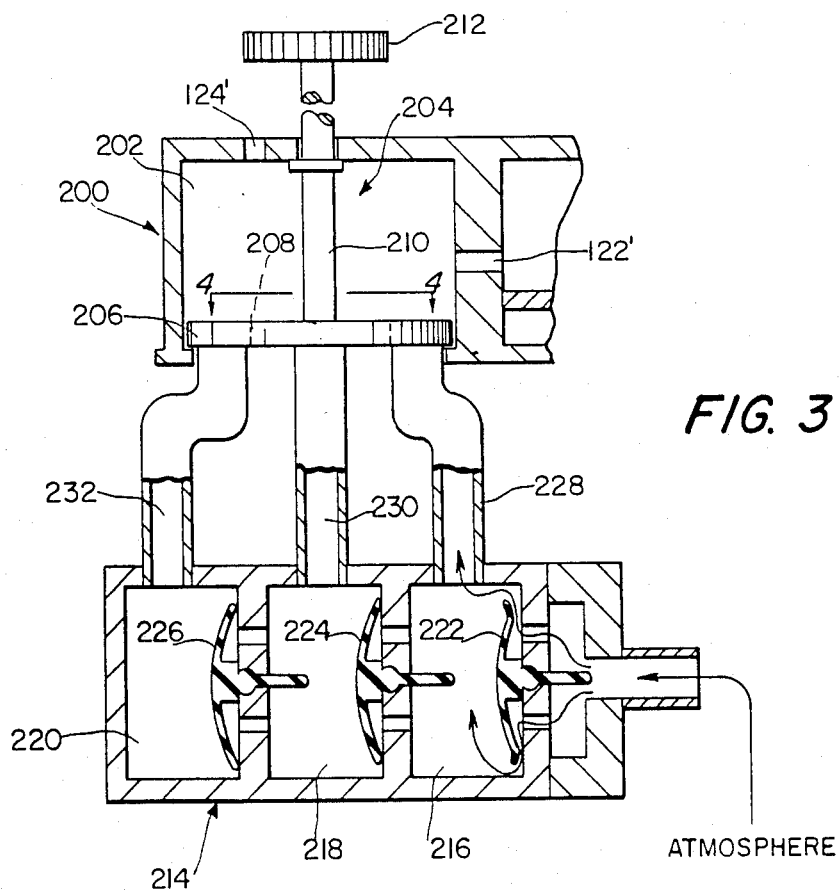
FIG. 3 is a front elevation view of a pressure varying control device which can be used in place of the pressure varying control device depicted in FIG. 2.
Figure 4:
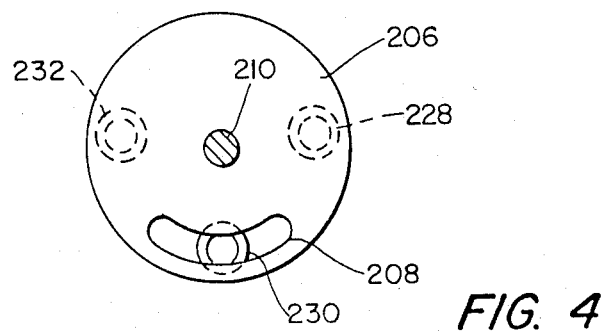
FIG. 4 is a top plan view of the valve member depicted in FIG. 3.

Depicted in FIG. 3 is an alternative embodiment of a secondary control chamber 200 which can be used in place of secondary control chamber 112 in drainage apparatus 10. In this embodiment, secondary control chamber 200 includes a suction side 202 which corresponds to suction side 114 of secondary control chamber 112 and includes an opening 124' connected to suction outlet 18 and a restricted opening 122' connected to suction side 86 of primary control chamber 84. Instead of an adjustable umbrella valve 118 as with secondary control chamber 112, secondary control chamber 200 is provided with a valve selector 24. Valve selector 204 includes a circular valve member 206 which is shown in greater detail in FIG. 4. Valve member 206 includes an arcuate slot 208 therethrough. Attached at the center of valve 206 is a stem 210 which extends through secondary control chamber 200 and the top of container 12 to terminate in a handle 212.

Located beneath valve selector 204 is a series valve member 214. Series valve member 214 is divided into three chambers 216, 218 and 220. Mounted in each chamber 216, 218 and 220 is a resiliently biased umbrella valve 222, 224, and 226, respectively. Each chamber 216, 218, and 220 also includes a passage 228, 230, and 232, respectively, which terminates at one side of valve member 206. As shown best in FIG. 4, passages 228, 230 and 232 are equally spaced around the center of valve member 206 at a distance from the center of valve 206 equal to the distance of arcuate slot 208 from the center of valve member 206. It should be appreciated that valve member 206 is rotatable by handle 212 to position arcuate slot 208 over one of passages 228, 230 or 232. In addition, arcuate slot 208 is of such a length that at least one of passages 228, 230 or 232 lies underneath arcuate slot 208 at all times.

Series valve member 214 includes an inlet end 234 which is suitably vented to atmosphere such as by being vented to vent chamber 94 in container 12. Preferably, umbrella valves 222, 224, and 226 are substantially identical and open when a predetermined pressure differential exists across a respective umbrella valve 222, 224 or 226. This predetermined pressure differential is chosen at a convenient value, such as −20 centimeters of water. Thus, umbrella valve 222 only opens when the pressure in chamber 216 is less than −20 centimeters of water. Because umbrella valves 222, 224 and 226 are in series, umbrella valve 224 only opens when the pressure in chamber 218 is −20 centimeters of water less than the pressure in chamber 216. Thus, umbrella valve 224 only opens after umbrella valve 222 is opened and the pressure in chamber 218 is −40 centimeters of water. In the same manner, umbrella valve 226 opens only when the pressure in chamber 220 is −60 centimeters of water.

In operation, secondary control chamber 200 functions in the following manner when used in place of secondary control chamber 112 in drainage apparatus 10. Initially, it is determined what value of negative pressure is desired in collection chamber 14. Once this is determined, handle 212 is rotated by the user to rotate arcuate slot 208 of valve member 206 over a respective one of passages 228, 230 or 232. Preferably, some indicia (not shown) is provided on the top of container 12 to indicate which passage 228, 230 or 232 is connected to suction side 202 when handle 212 is at a particular position.

Where passage 228 is connected to suction side 202 by movement of valve 206, the value of negative pressure created in suction side 202 is equal to approximately −20 centimeters of water assuming the source of suction is greater than −20 centimeters of water. This will cause a slightly reduced pressure in collection chamber 14 as the pressure in collection chamber 14 will be somewhat further reduced by the bleeding of air through primary control chamber 84. If it is desired to increase the negative pressure in collection chamber 14, handle 212 is rotated to a position where chamber 218 is connected to suction side 202. This will cause the pressure in suction side 202 to increase to −40 centimeters of water and the negative pressure created in collection chamber 14 to correspondingly rise. Finally, the selection of passage 232 causes the negative pressure in suction side 202 to increase to −60 centimeters of water and the negative pressure in collection chamber 14 to also change accordingly.

It should be appreciated that due to the construction of arcuate slot 208, there is no position which valve selector 204 can be rotated to where none of passages 228, 230 or 232 is connected to suction side 202. The design of arcuate slot 208 in this manner is to prevent valve selector 204 from ever being moved to a position where no atmospheric air is bled into suction side 202 so that the full force of the source of negative pressure is applied to primary control chamber 84 and hence to collection chamber 14.

Figure 5:
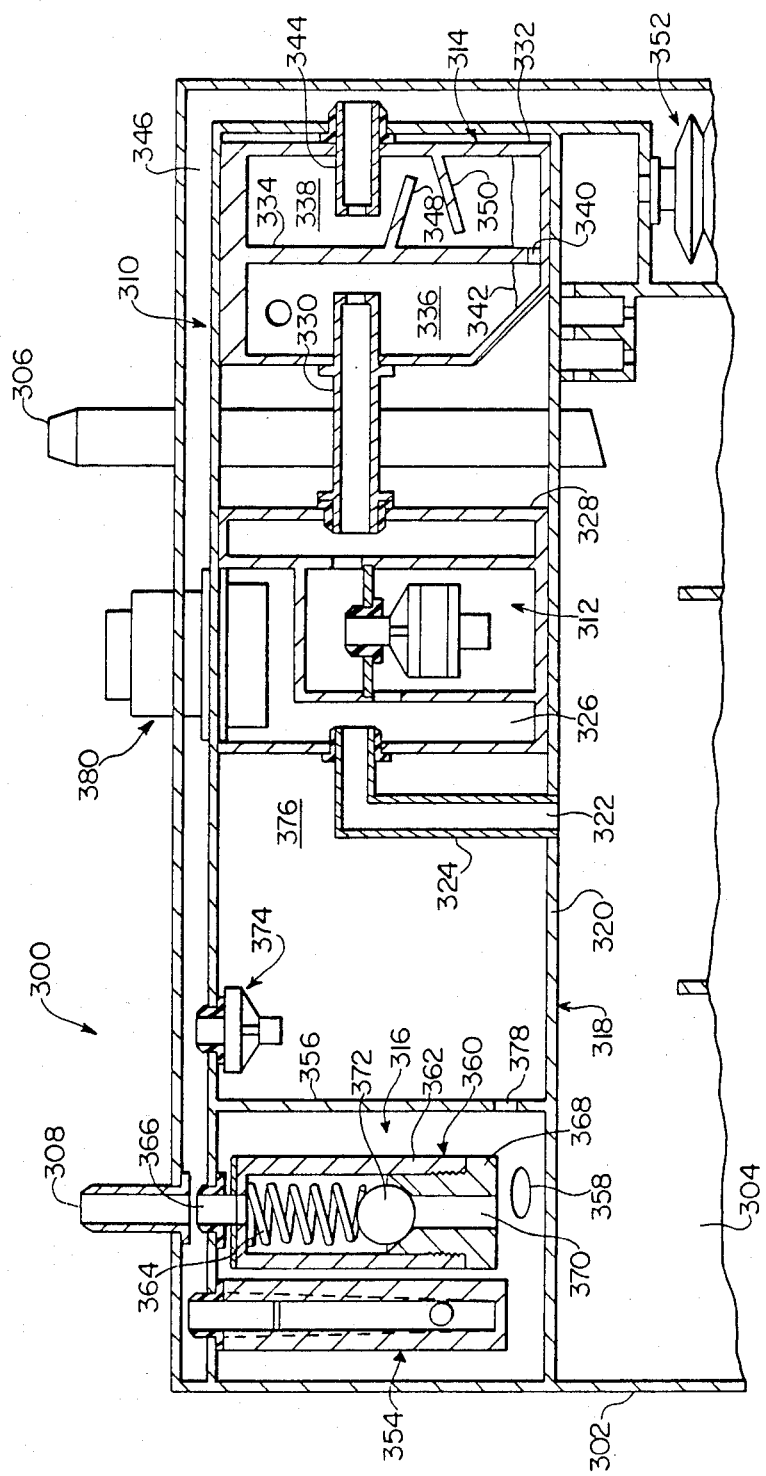
FIG. 5 is a front elevation view in cross section of the upper portion of an alternative embodiment of a drainage apparatus according to the present invention.

Depicted in FIG. 5 is an alternative embodiment of a drainage apparatus 300 which is broadly similar to drainage apparatus 10. Drainage apparatus 300 includes a container 302 in which a collection chamber 304 is located. A fluid inlet 306 is provided into chamber 304 and a suction outlet 308 is also provided in communication with collection chamber 304. Suction outlet 308 is connected to collection chamber 304 by a passageway 310 which includes a non-fluid passageway one-way valve means 312, an air leak indicating means 314, and a suction control means 316.

Drainage apparatus 300 also includes an upper chamber 318 which is separated from collection chamber 304 by an interior wall 320. A suction inlet 322 is provided in interior wall 320 which is connected by a short passage 324 to a tell-tale chamber 326. Tell-tale chamber 326 is fluidly connected to one-way valve means 312 which is located in a valve chamber 328. One-way valve means 312 is substantially the same as one-way valve means 24 of drainage apparatus 10 described above so that only flow upwards through one-way valve means 312 is allowed. A short passage 330 connects valve chamber 328 to air leak indicating means 314.

Air leak indicating means 314 functions in a similar manner to flow indicating means 26 of drainage apparatus 10. However, air leak indicating means 314 is somewhat differently constructed. As shown in FIG. 5, air leak indicating means 314 includes a chamber 322 having a central wall 334 extending downwardly through the center thereof to divide chamber 322 into an inlet side 336 and outlet side 338. At the bottom of central wall 334 is an aperture 340 which provides fluid communication between inlet side 336 and outlet side 338. Normally, the bottom of chamber 332 contains a liquid 342 which covers aperture 340.

As shown, short passage 330 extends from valve member 328 to a central portion of inlet side 336. Similarly, a short passage 334 extends from a central portion of outlet side 338 to elongate passage 346. By extending centrally of inlet side 336 and outlet side 338, respective short passages 330 and 344 do not allow liquid 342 to enter therein no matter how drainage apparatus 300 is tipped. In other words, the ends of short passages 330 and 344 inside of air leak indicating means 314 extend into respective inlet side 336 and outlet side 338 so as to be beyond the fluid level no matter in which direction drainage apparatus 300 is tipped (sideways, upside down etc.) as may occur during skipping. It should also be appreciated that outlet side 338 is provided with baffle plates 348 and 350 so that gases bubbling in liquid 342 through aperture 340 do not carry liquid into short passage 344. As with air leak indicating means 26 of drainage apparatus 10, air leak indicating means 314 is similarly viewable from the outside of drainage apparatus 300 so that the bubbling of air through aperture 340 serves as a visible indication of flow therethrough.

Elongate passage 346 is fluidly connected to a dynamic pressure measuring means 352 which is substantially the same as dynamic pressure measuring means 150 of drainage apparatus 10 and thus will not be described further. Elongate passage 346 also fluidly connects to suction outlet 308 which is operably associated with control means 316 and a pressure measuring means 354. Pressure measuring means 354 is substantially similar to pressure measuring means 100 of drainage apparatus 10 and will not be described further.

Control means 316 is disposed in a control chamber 356 which is vented to atmosphere by an aperture 358. Control means 316 includes a biased valve means 360 as shown. Biased valve means 360 includes a valve body 362 having a spring 364 disposed therein adjacent a valve outlet 366. Threadably received in the other end of valve body 362 is a valve seat 368 having a bore 370 therethrough. As shown spring 364 seats a ball 372 against valve seat 368.

In operation, control means 316 functions in the following manner. With suction outlet 308 connected to a predetermined constant source of negative pressure, this negative pressure is exerted on biased valve means 360 through valve outlet 366. This causes ball 372 to be moved against the force of spring 364 away from valve seat 368. In this position, atmospheric air is admitted through biased valve means 360 from aperture 358 directly to suction outlet 308. As there is some resistance to flow through biased outlet 360, a portion of the suction exerted on suction outlet 308 is not compensated for by the flow of atmospheric air through biased valve means 360. This portion of the suction is then conducted through passageway 310 to collection chamber 304.

By an appropriate design of the resiliency of spring 364 and the location of valve seat 368 relative to spring 364, the portion of the suction applied to collection chamber 304 can be maintained relatively constant. Preferably, the adjustment of the location of valve seat 368 relative to spring 364 is performed at the factory and is easily accomplished by threadably adjusting valve seat 364 forward or backward relative to valve body 362. If desired, a control means including two biased valve means connected in series and including a restricted opening similar to control means 28 can be used.

Drainage apparatus 300 is also provided with a positive pressure relief valve means 374. Positive pressure relief valve means 374 is similar in construction to positive pressure relief valve means 140 of drainage apparatus 10. Positive pressure relief valve means 374 is connected to collection chamber 304 through passageway 310. In particular, positive pressure relief valve means 374 is disposed in a chamber 376 adjacent control chamber 356. Chamber 276 is in fluid communication with atmosphere through an aperture 378 and aperture 358. Thus, where a positive pressure exists in collection chamber 304 (for example, above 0.5 cmH$_2$O), this pressure is conducted through passageway 310 and is automatically relieved through positive pressure relief valve means 374 to atmosphere. However, it should be appreciated that any failure of positive pressure relief valve means 374 does not destroy the operation of drainage apparatus 300 as any air leaking through positive pressure relief valve means 374 is prevented from reaching collection chamber 304 by one-way valve means 312. Instead, any air which might leak past positive pressure relief valve means 374 is withdrawn through suction outlet 308 and due to the operation of control means 316 this leaking air should not effect the suction applied to collection chamber 304.

Drainage apparatus 300 also includes an excess negative pressure relief means 380 which is similarly constructed to excess negative pressure relief means 130 of drainage apparatus 10. In this embodiment, excess negative pressure relief means 380 is disposed in tell tale chamber 326 so that excess negative pressure relief means 380 is exposed to the negative pressure in collection chamber 304 through short passage 324.

The details of the construction of excess negative pressure relief means 380 are shown in greater detail in FIGS. 6, 7, and 8. As shown in these figures, excess negative relief means 380 includes a valve body 328 having a seating surface 384. Located adjacent seat surface 384 is a plunger 386 having an O-ring 388 disposed along the surface of plunger 386 adjacent seating surface 384. Plunger 386 also includes a stem 390 which extends through an aperture 392 in seating surface 384. Attached to stem 390 is a push button 394.

As shown, plunger 386 is spring biased so that O-ring 388 contacts seating surface 384 by a spring 396. Spring 396 presses against a member 398 attached to the lower end of valve body 382. As shown, member 398 has an aperture 400 therein. With this construction, push button 394 is normally biased by spring 396 into the position where O-ring 388 contacts seating surface 384 and any flow through valve body 382 is prevented.

Also attached to the bottom of valve body 382 is a one way valve means 402. One-way valve means 402 includes a valve body 404 having a central aperture 406 and four apertures 408 located therein. The top of valve body 404 is spaced from the bottom of member 398 to provide for the flow of air between apertures 408 and aperture 400.

One-way valve means 402 also includes an umbrella valve 410 whose stem 412 is received in central aperture 406 as shown in FIG. 6. The umbrella portion of umbrella valve 410 then extends out over apertures 408. Located below umbrella valve 410 is a filter assembly 414 including a filter cover 416, a filter 418, and a filter bottom 420. As shown in FIG. 8, filter cover 416 is preferably formed of a spiral and spoked pattern to allow a maximum flow of air through filter 418. Filter bottom 420 also includes an aperture 422 therein.

In operation, excess negative pressure relief means 380 functions in the following manner. Initially, spring 396 presses plunger 386 with sufficient force to assure that O-ring 388 is maintained in contact with seating surface 384 despite any negative pressure existent in suction chamber 304. However, should an excess negative pressure exist in collection chamber 304, the physician or operator of drainage apparatus 300 acts to relieve this excess negative pressure by depressing push button 394. As soon as push button 394 is depressed, plunger 386 is moved downwardly so that O-ring 388 is no longer in contact with seating surface 384. This allows atmospheric air to pass around push button 394 and stem 390 through aperture 392. The atmospheric air then exerts a pressure on umbrella valve 410. Umbrella valve 410 is chosen so as to require a predetermined difference in pressure on either side of umbrella valve 410 before umbrella valve 410 will open. Thus, if the excess negative pressure on the collection chamber side of umbrella valve 410 is sufficient, the air at atmospheric pressure entering valve body 382 is sufficient to open umbrella valve 410 as well and pass through apertures 408 to relieve the excess negative pressure in collection chamber 304.

It should also be appreciated that excess negative pressure relief means 380 operates only to relieve the excess negative pressure in collection chamber 304 and not to destroy all negative pressure therein. Thus, where a negative pressure of $-20$ cmH$_2$O is desired in collection chamber 304, umbrella valve 410 is chosen such that umbrella valve 410 closes when the difference in pressure between atmosphere in collection chamber 304 is $-20$ cmH$_2$O. Therefore, when relieving excess negativity in collection chamber 304 by the depression of push button 394, umbrella valve 410 automatically closes when sufficient air has been admitted into collection chamber 304 to relieve the excess negativity down to the $-20$ cmH$_2$O level when suction is applied. If no suction is applied, excess negativity is reduced to $-10$ cmH$_2$O.

Depicted in FIG. 9 is an alternative embodiment of a control means 430 which can be used in place of control means 316 of drainage apparatus 300. In this embodiment, control means 430 includes a gross pressure adjusting means 431 including a gross biased valve means 432 and a fine pressure adjusting means 433 including a fine biased valve means 434. As shown, fine biased valve means 434 is substantially similar to biased valve means 360 described above. Thus, fine biased valve means 434 includes a ball 436 which is spring biased into position against a valve inlet 438. At the other end, fine biased valve means 434 includes a passageway inlet 440 which is fluidly connected to passageway 310 and hence collection chamber 304 of drainage apparatus 300. Located between valve outlet 438 and passageway inlet 440 is a valve outlet 442. Valve outlet 442 includes a bore 444 of limited size to restrict the flow of gases through bore 444.

Bore 444 communicates with the interior of gross biased valve means 432. Gross biased valve means 432 includes a ball 446 which is biased against a valve inlet 448. At the other end, gross biased valve means 432 includes a valve outlet 450 which is directly connected to suction outlet 308 of drainage apparatus 300. It should be appreciated that both valve inlet 438 and valve inlet 448 are fluidly connected to atmosphere through aperture 358 in drainage apparatus 300. It should also be appreciated that valve outlet 450 has a relatively small diameter so that the flow of fluids through valve outlet 450 is also restricted.

In operation, control means 430 functions in the following manner. When suction outlet 308 is connected to a suitable source of suction, ball 446 is immediately raised off of valve inlet 448 by the applied suction. The spring biasing of ball 446 is sufficient to create a negative pressure in gross biased valve means 432 of slightly more than $-20$ cmH$_2$O. This negative pressure of slightly more than $-20$ cmH$_2$O is then applied through bore 444 to the interior of fine biased valve means 434. The spring biasing of ball 436 and the adjustment of valve inlet 438 is then designed to cause the pressure within fine biased valve means 434 to achieve a steady state negative pressure of approximately $-20$ cmH$_2$O. This negative pressure is then exerted through passageway inlet 440 to collection chamber 304. By the use of two biased valve means, a greater degree of accuracy in control of the negative pressure within the collection chamber is achieved. In addition, the restriction of bore 444 and valve outlet 450 similarly assures that not too great a negative pressure is exerted on collection chamber 304 despite any changes in suction at suction outlet 308.

In experiments performed with such a biased valve control means, it has been found that for an applied suction at suction outlet 308 from 20 mmHg to 200 mmHg, a negative pressure in the collection chamber of $-20$ cmH$_2$O + 1 cmH$_2$O can be achieved.

Depicted in FIGS. 10 and 11 is an alternative embodiment of an air leak indicating means 460 which can be used in place of air leak indicating means 314 in drainage apparatus 300 or air leak indicating means 26 in drainage apparatus 10. Air leak indicating means 460 is used to indicate not only flow by the quantitative value of this flow. Air leak indicating means 460 is similar to the flow indicating means disclosed in U.S. Pat. No.

3,782,497 (Bidwell et al) which is herein incorporated by reference. Air leak indicating means 460 includes an air leak chamber 462 which is divided into an inlet side 464 and an outlet side 466 by a wall 468. Bottom wall 470 of air leak chamber 462 is also slanted at about a 6 degree angle as shown. Inlet side 464 is fluidly connected to short passage 330 while outlet side 466 is fluidly connected to short passage 344 as shown.

Inlet side 464 is separated from outlet side 466 by wall 468 and by a divider member 472 which is spaced above bottom wall 470 and parallel thereto. As shown, member 472 includes a plurality of vertical apertures 474 spaced along the length thereof. Located above member 472 and between adjacent apertures 474 is a plurality of vanes 476. Located between vanes 476 and short passage 344 is a baffle 478 as shown. It should also be appreciated that a liquid 480 is provided in flow chamber 462.

In operation, air leak indicating means 460 functions in the following manner. As gases are withdrawn through short passage 330 to short passage 344 by the operation of drainage apparatus 300, these gases bubble through liquid 480. Initially, the gases pass through aperture 474 which is uppermost in member 472. However, as the flow of gases increases, the gases additionally flow through succeeding lower apertures 474 along the length of member 472. Thus, as explained in the above-identified patent, the number of apertures 474 through which gases bubble, or rather the lowermost of the apertures 474 through which the gases bubble, indicates the volume of flow through air leak indicating means 460. Suitable indicia (not shown) are be provided on the outside of drainage apparatus 300 to indicate this to the user. It should also be appreciated that baffle 478 prevents any bubbles which are formed by the gases passing through liquid 480 and apertures 474 from being drawn into short passage 344.

Although the present invention has been described with respect to exemplary embodiments thereof, it will be understood by those of ordinary skill in the art that variations and modifications can be effected within the scope and spirit of the invention.

What is claimed is:

1. A suction control device for maintaining a relatively constant negative pressure in a collection chamber of a drainage apparatus over wide variations in applied suction, comprising:
   a first passageway to the collection chamber and a second passageway to a source of suction,
   a fine pressure adjusting means for finely adjusting the pressure in said collection chamber including a first chamber and a resiliently biased fine one-way valve disposed in said first chamber so as to divide said first chamber into a vent side which is vented to atmosphere and a suction side which is fluidly connected to said first passageway to the collection chamber, said fine one-way valve permitting fluid flow only from said vent side to said suction side when the negative pressure in the collection chamber slightly exceeds a desired value;
   a gross pressure adjusting means for grossly adjusting the pressure in said collection chamber including a second chamber and a resiliently biased gross one-way valve disposed in said second chamber so as to divide said second chamber into a vent side which is vented to atmosphere and a suction side which is fluidly connected to the said second passageway to a source of suction and downstream of said suction side of said first chamber, said gross one-way valve variably permitting a sufficient gross air flow from said vent side to said suction side of said second chamber to maintain the negative pressure in said suction side of said second chamber at a value slightly greater than the desired value for the collection chamber over a wide range of applied surfaces whereby this negative pressure is applied to said suction side of said first chamber where the negative pressure is slightly reduced to the desired value which is in turn applied to the collection chamber, and a third passage way interconnecting the suction sides of said first and second chambers whereby fluid flow passes from the collection chamber through said first passageway and said first chamber into said second chamber and to said source of suction througuh the second passageway.

2. A suction control device as claimed in claim 1 said third passageway including restrictor means for restricting the flow of gases through said passage.

3. A suction control device as claimed in claim 2 wherein said suction side of said second chamber is directly connected to applied suction through an outlet passage and further including a restrictor means disposed in said outlet passage for restricting the flow of gases through said passage.

4. A suction control device as claimed in claim 3 wherein said fine one-way valve and said gross one-way valve include a respective spring-biased ball which divides said respective first and second chambers.

5. A suction control device as claimed in claim 1 wherein said one-way valve includes an adjusting means for adjusting the value of desired pressure at which said fine-way value permits fluid flow from said vent side to said suction side of said first chamber.

* * * * *